(12) United States Patent
Quenzer et al.

(10) Patent No.: US 7,286,294 B2
(45) Date of Patent: Oct. 23, 2007

(54) BEAM-SHAPING ELEMENT FOR OPTICAL RADIATION AND A METHOD FOR PRODUCING SAID ELEMENT

(75) Inventors: Hans-Joachim Quenzer, Itzehoe (DE); Wolfgang Reinert, Neumünster (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 135 days.

(21) Appl. No.: 10/484,214

(22) PCT Filed: Jul. 17, 2002

(86) PCT No.: PCT/DE02/02617

§ 371 (c)(1),
(2), (4) Date: Aug. 5, 2004

(87) PCT Pub. No.: WO03/009432

PCT Pub. Date: Jan. 30, 2003

(65) Prior Publication Data
US 2004/0246609 A1    Dec. 9, 2004

(30) Foreign Application Priority Data
Jul. 18, 2001    (DE) .................. 101 34 893

(51) Int. Cl.
*G02B 1/10*    (2006.01)
*F21V 9/04*    (2006.01)

(52) U.S. Cl. .............. 359/586; 359/359; 359/577
(58) Field of Classification Search ........ 359/350–361, 359/577–590; 438/52–53
See application file for complete search history.

(56) References Cited

U.S. PATENT DOCUMENTS

| 5,437,947 A | * | 8/1995 | Hur et al. ..................... 430/5 |
| 5,589,283 A | * | 12/1996 | Iwasaki et al. ............. 428/812 |
| 5,961,861 A | | 10/1999 | McCay et al. ......... 219/121.83 |
| 6,020,215 A | * | 2/2000 | Yagi et al. .................... 438/52 |
| 6,042,682 A | * | 3/2000 | Funaya et al. ........... 156/273.3 |
| 6,061,323 A | | 5/2000 | Jerman et al. ........... 369/13.12 |
| 6,101,164 A | * | 8/2000 | Kado et al. ................. 369/126 |

FOREIGN PATENT DOCUMENTS

| EP | 1 191 360 | 3/2002 |
| WO | WO 01/28478 | 4/2001 |

* cited by examiner

*Primary Examiner*—Thong Q Nguyen
(74) *Attorney, Agent, or Firm*—Venable, LLP; Robert Kinberg; Marina V. Zalevsky

(57) ABSTRACT

A beam-shaping element comprises a carrier substrate (1) bearing a thin-layer metallization which is structured for shaping the beam of optical radiation. The thin-layer metallization includes at least two metallic layers (2, 3), which, upon impingement of the optical radiation (4), react with each other accompanied by a permanent change in color in response to a certain intensity and/or an irradiation period of the optical radiation (4).

12 Claims, 2 Drawing Sheets

BEAM-SHAPING ELEMENT FOR OPTICAL RADIATION AND A METHOD FOR PRODUCING SAID ELEMENT

TECHNICAL FIELD OF APPLICATION

The present invention relates to a beam-shaping element for optical radiation, in particular for UV-laser radiation, comprising a carrier substrate bearing a thin-layer metallization which is structured for shaping the beam of the incident optical radiation. The invention also relates to a method for producing a beam-shaping element for optical radiation.

Beam-shaping elements are utilized, for example, for shaping laser beams for applications in material processing or even in medical technology. The purpose of beam-shaping elements is primarily to generate a prescribed intensity profile of the laser radiation which is advantageous for the respective application. Beam-shaping elements can be utilized, for example, for leveling the intensity of the profile of intensive UV laser radiation in order to be able to generate continuous transition to the unprocessed areas in planar material processing. The processed material can also be of a living nature. In particular, in the field of medicine, for example cornea treatment with a UV laser requires such a continuous transition to correct cornea aberrations. The beam-shaping element is designed as a microstructured beam-shaping diaphragm at whose microstructures the incident intensity profile of the laser radiation is diffracted to obtain a desired flat beam profile. In such type beam-shaping elements, a thin metallic layer is applied onto a transparent carrier substrate in which the microstructures are generated.

In particular, when using intensive UV laser radiation, however, this metallization is impaired with time so that the effect of the beam-shaping on the incident laser radiation is no longer predictable, which can lead, particularly in the field of medicine, to considerable risk for the patient, because the user does not notice early wear of the metallization. For these reasons, beam-shaping elements should only be used once in the field of medical technology for intensive UV radiation. However, to ensure such single use requires that the user works with painstaking care, because it is usually not evident that the beam-shaping element has been previously used. It can, therefore, occur that an already used beam-shaping element is accidentally repeatedly employed.

The object of the present invention is to provide a beam-shaping element for optical radiation, in particular, for UV laser radiation, as well as a method for producing a beam-shaping element on which single use can be recognized when employing it in intensive optical radiation.

SUMMARY

The object of the present invention is solved with a beam-shaping element comprising a carrier substrate bearing a thin-layer metallization which is structured for shaping the beam of the optical radiation is distinguished in that the thin-layer metallization is composed of at least two metallic layers, which interact when the optical radiation of a certain intensity and/or irradiation period occurs resulting in a permanent change in color.

BRIEF DESCRIPTION OF THE DRAWINGS

The present invention is briefly explained once more in the following, without limitation of the overall inventive idea, using preferred embodiments with reference to the accompanying drawings.

FIGS. 4(a)-4(f) show an exemplary course of the production of a beam-shaping element according to FIG. 1;

WAYS TO CARRY OUT THE INVENTION

Figure 1:
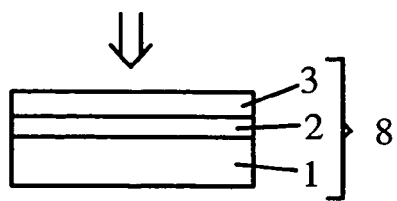
FIG. 1 shows a cross section of an example of a set up of a beam-shaping element of the present invention.

The present beam-shaping element, comprising a carrier substrate bearing a thin-layer metallization which is structured for shaping the beam of the optical radiation, is distinguished in that the thin-layer metallization is composed of at least two metallic layers, which interact when the optical radiation of a certain intensity and/or irradiation period occurs resulting in a permanent change in color.

The reaction of the materials of the two metallic layers preferably leads to formation of an alloy of the respective metals as a result of the incident optical radiation causing these layers to become warm at the point of impact of the optical radiation. Suited selection of respective metals causes the alloy formation to distinctly change color in comparison to the color of the upper metallic layer. Suited metals for such type alloy formation involving a change in color are common knowledge to someone skilled in the art. The energy required to trigger the reaction should, of course, lie distinctly above the thermal energy without irradiation of the optical radiation. Furthermore, the intensity and the period of irradiation with the optical radiation, at which the reaction is triggered, must not be so high that the metallic layers become damaged at this intensity and/or during this period of irradiation.

When using the present beam-shaping element for shaping the intensity profile of optical radiation, in particular of laser radiation, which has sufficient intensity, was irradiated for a sufficient irradiation period, the user can recognize immediately after use, by the change in color at the point of impact of the optical radiation, that the beam-shaping element has been previously employed. In this way, errors caused by multiple use of beam-shaping elements can be prevented when employing intensive UV laser radiation, particularly, in the field of medical technology. The traces of use caused by the change in color at the point of impact of the irradiation indicate optically possible wear of the metallization long before the metallization shows cracks or holes caused by radiation ablation. Despite these optically visible traces of use, the functionality of the metallization of the beam-shaping element is retained so that at this point no cracks or bonding problems occur in the metallization.

Preferably, the metallic layers in the present beam-shaping element are selected in such a manner that the reflectivity of the thin-layer metallization for the utilized optical radiation is permanently lowered by the triggered reaction between the two layers. This further reduction of reflection in the discolored area increases the longevity of the upstream high-grade optic, which can easily be damaged if reflection at the beam-shaping element is too high, in particular when using UV laser radiation.

In a preferred embodiment of the present invention, the upper of the two metallic layers is formed of a noble metal. The use of this covering layer of a noble metal permits unlimited aging of the beam-shaping element so that the aging causes no malfunctions. The lower of the two metallic layers, i.e, the layer lying on the carrier substrate, is preferably formed of chrome or a chrome alloy. Chrome has numerous advantages in this connection. For instance, it can act as a bonding agent between the carrier substrate and the upper layer. On the other hand, this material permits wet-chemical etching quite readily for generating the microstructuring required for beam shaping.

In the preferred embodiment of the beam-shaping element, the upper layer is formed of gold and the lower one of chrome, with the layer-thickness ratio of the chrome layer and the gold layer being in the range of 1:1.4 to 1:1.8.

When irradiated with intensive optical radiation, in particular using UV laser radiation, these two metallic layers form an alloy as a result of a local metallurgical reaction due to the irradiation, leading to a distinctly visible discoloring from lustrous gold to mat gray-brown at the point of impact of the optical radiation. Suited selection of the layer-thickness ratio permits formation, on the one hand, of a suited alloy and, on the other hand, prevents great tensile stress in the thin-layer metallization due to alloy formation. This beam-shaping element can be particularly advantageously employed in combination with UV laser radiation in the 193 nm range as, in this laser radiation wavelength range, the optically visible discoloring leads to continuously diminishing reflectivity to below 1%. Whereas, prior to impingement of the laser beam, the reflectivity of the gold layer is approximately 10% at 193 nm.

Thin-layer metallization composed of at least two metallic layers must, of course, be selected so thick that the optical denseness required for beam shaping is obtained. However, preferably, this thin-layer metallization has an overall thickness of $\leq 250$ nm so that microoptical structuring with structure widths below 250 nm can be achieved.

In the present method for producing a beam-shaping element for optical radiation, in particular a beam-shaping element according to the preceding description, first a lower layer of chrome or of a chrome alloy is applied onto a carrier substrate that is transparent for the optical radiation. Then an upper layer of a noble metal is applied—under circumstances after application of an intermediate layer—over this lower layer. The resulting sequence of layers is then structured for the required beam shaping. Structuring occurs by microstructuring of the upper layer using photolithography and a subsequent dry etching process conducted etching down to the lower layer. The upper layer acts then as an etching mask for microstructuring of the lower layer, which then occurs by means of a wet-chemical etching process. By this means, the beam-shaping diaphragm with a precise microstructure can be produced in a simple manner. The lower and the upper layer are preferably applied using a physical sputtering method The present method permits production of a beam-shaping element as described in the preceding description. However, the method can also be utilized to produce beam-shaping elements which do not show traces of use by discoloring upon impingement of optical radiation. In this case, the applied layers are thermodynamically stabilized by means of a thermal aging process, in particular by tempering, in such a manner that no optically visible metallurgical reaction occurs any longer upon impingement of the optical radiation. Due to the thermal aging process, if gold is employed as the upper layer and chrome as the lower layer, under circumstances with a titanium intermediate layer, very little reflectivity of <2% is achieved for optical radiation in the range of 193 nm in an advantageous manner, which does not even change under laser impingement. Moreover, due to the covering layer of a noble metal, a beam-shaping element with infinite aging time at room temperature is yielded. Such a type beam-shaping element can be used in fields in which a multiply-used beam-shaping element with little reflectivity and good durability is desired.

FIG. 1 shows schematically an example of a set up of a beam-shaping element 8 as realized in the present invention. In this example the beam-shaping element 8 is composed of the carrier substrate 1 with a thin-layer metallization of two metallic layers 2,3 located on it. In this example, a quartz glass polished on both sides is employed as the carrier substrate 1, because transmission is very high in this quartz glass in the range of the utilized UV radiation, in particular in the 193 nm range. A chrome layer, which acts as a bonding agent for the upper layer to the quartz substrate, is applied as the lower layer 2. The upper metallic layer 3 is of gold, which has a low reflectivity of approximately 10% at the laser wavelength of 193 nm employed in this example. In this example, the overall layer thickness of the thin-layer metallization is 140 nm, with the lower layer 2 of chrome 40 nm thick and the upper layer 3 of gold 100 nm thick or with a lower to upper layer ratio of 1:2.5. These layer thicknesses permit microstructuring of the thin-layer metallization with structure widths of up to 250 nm, which, however, is not shown in this figure. In one embodiment, the thin-layer metallization is structured to form an optical diaphragm, e.g, a hole for the impinging optical radiation.

Figure 2:
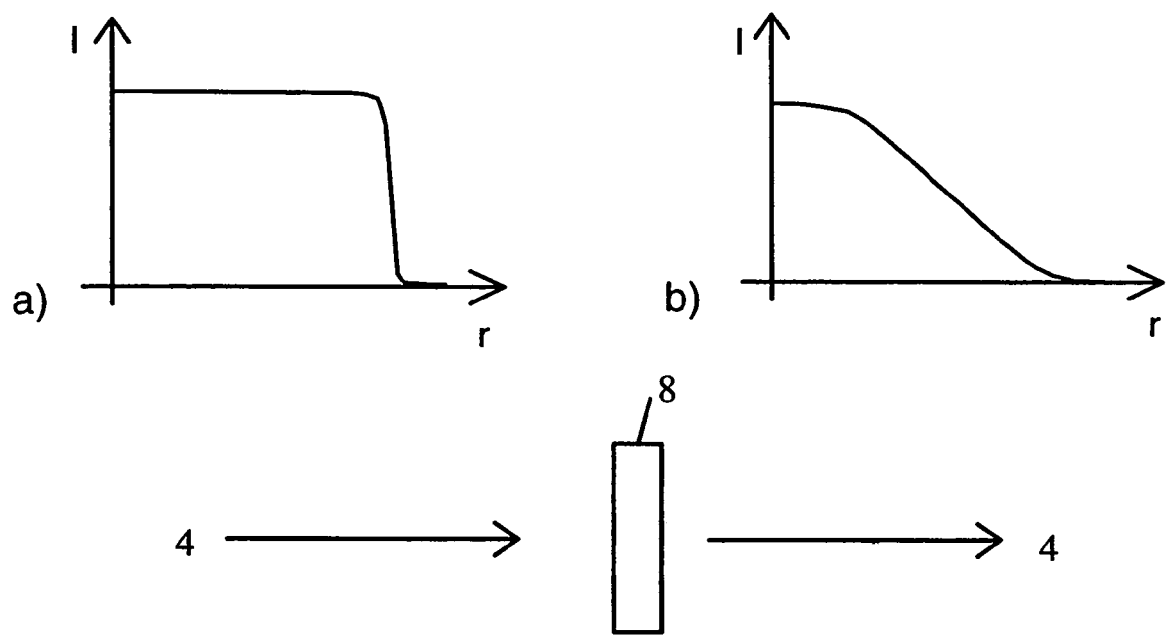
FIG. 2 shows an example of a change in an intensity profile of a laser beam passing through a beam shaping element.

FIG. 2 shows in detail a) an example of an intensity profile of a UV laser beam 4, which the beam-shaping element 8 is to alter. The shape of the intensity profile is approximately rectangular, so that there is a steep drop in intensity at the beam boundaries. This drop is undesirable in many material processing applications. The beam-shaping element 8 can be microstructured according to the present invention in such a manner that the intensity profile of the impinging and passing UV laser beam 4 is leveled off and shows a continuous leveled off course at the beam boundaries, as detail b) shows as an example.

The geometry of the microstructures of the thin-layer metallization required for such a beam shaping can be calculated in advance while taking into account optical principles.

Figure 3:
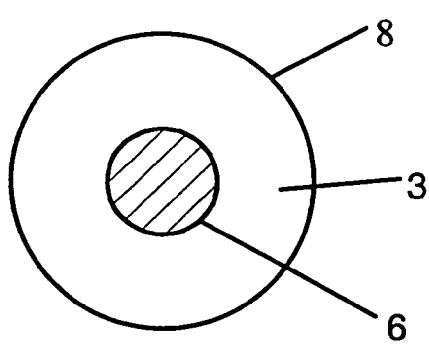
FIG. 3 shows a top view of a beam-shaping apparatus to illustrate an example of a visible trace of use in accordance with the present invention.

When utilizing beam-shaping element 8, as shown by way of example in FIG. 1, for shaping the beam of an intensive UV laser beam with a wavelength of 193 nm, as is for example utilized in the field of medicine in eye surgery, after the first use distinctly visible traces of use remain on the surface of the thin-layer metallization. FIG. 3 shows, as an example, a top view of such a beam-shaping element 8 on the thin-layer metallization. Bombardment with the UV laser radiation triggers a local metallurgical reaction between the gold and the chrome at the point of impact 6. This reaction causes optically visible discoloring of the surface of the lustrous gold (Au) to a mat gray-brown (Au—Cr alloy). This discoloring occurs only at the point of impact 6 of the laser radiation, whereas the remaining area of the surface retains its lustrous gold color. In this manner, it is always immediately noticeable if the beam-shaping element 8 has already been used. In the present case, the optically visible discoloring leads to a distinctly lower reflectivity of the UV laser radiation of below 1% compared to the initial starting state. Despite visible traces of use, the functionality of the metallization continues so that neither cracks nor bonding problems occur in the metallization.

Figures 4, 5:
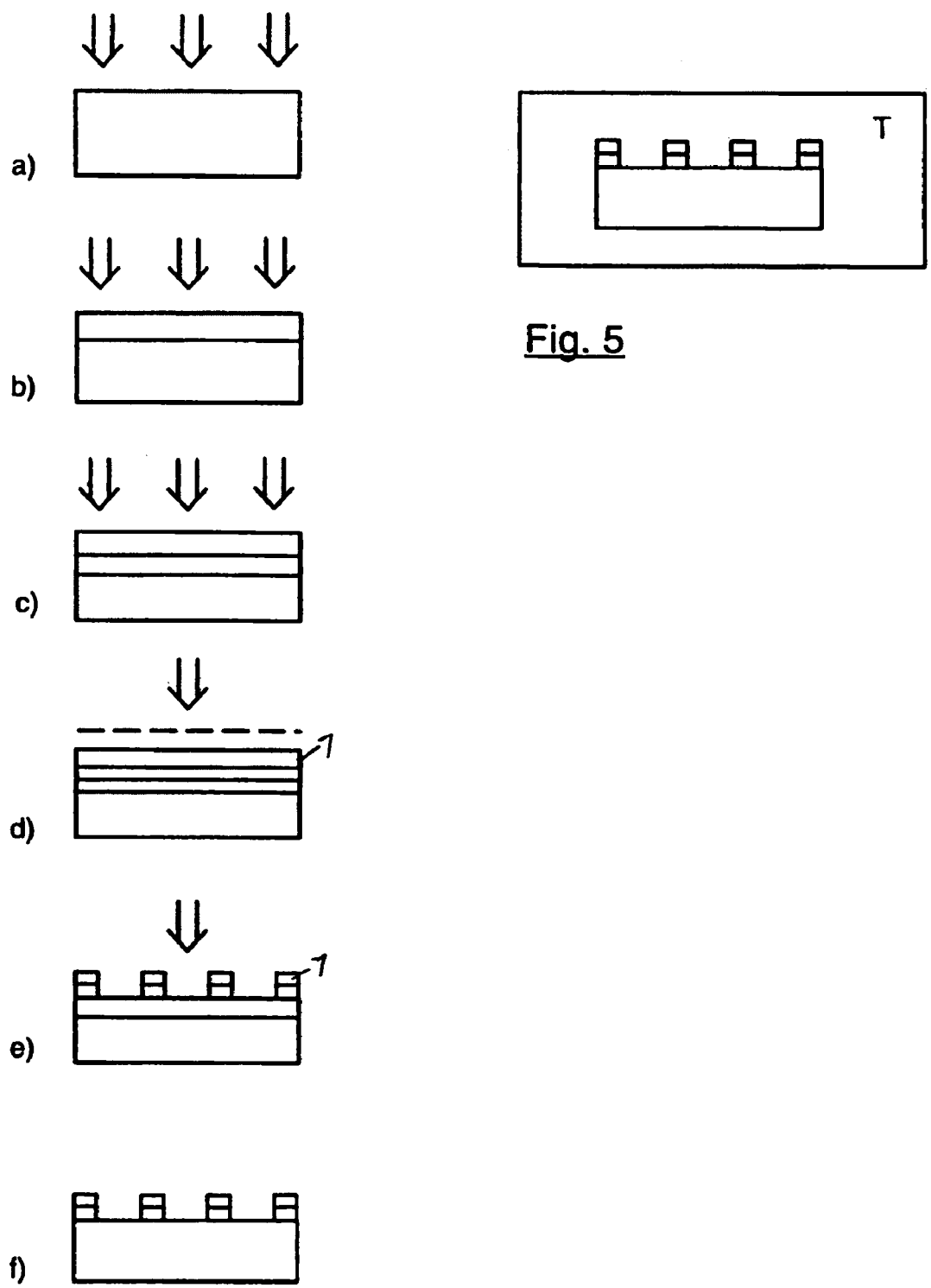
FIG. 5 shows a further example of the production of a beam-shaping element, that does not leave any optically visible traces of use.

FIG. 4 shows an example of different productions steps for producing a beam-shaping element 8 respectively a beam-shaping diaphragm according to FIG. 1. In this process, a 40 nm thick Cr layer 2 is applied onto a quartz wafer, that is polished on both sides (carrier substrate 1) and has a low surface roughness of <5 nm, by means of physical sputtering (FIG. 4 a/b). Without interrupting the vacuum, a 100 nm thick Au layer 3 is applied onto the Cr layer 2 also by means of physical sputtering leading to very good layer bonding (FIGS. 4a,b). Then a light-sensitive photoresist 7 is applied onto the thin-layer metallization formed by the two layers 2,3 (FIG. 4 c/d). Using a projection system, the photoresist layer 7 is selectively exposed with the aid of a mask to generate the desired microstructuring. After developing the photoresist film 7, the gold layer 3 is removed in the exposed areas using an argon plasma etcher and the chrome layer 2 is exposed (see FIG. 4 e/f). The chrome layer 2 is etched away at the exposed sites down to the quartz substrate 1 without roughening the quartz using a wet-chemical chrome etching solution. The structured gold layer 3 acts here as an etching mask in the wet-chemical etching process. After removal of the photoresist 7, the quartz wafer is divided into single beam-shaping elements 8 with a diamond cutting device.

By modifying this method, a beam-shaping element can also be produced that does not form optically visible traces of use and possesses low reflectivity and high resistance under UV laser bombardment. As shown in FIG. 5, for this purpose, the beam-shaping diaphragm produced using the method according to FIG. 4 is then also thermodynamically stabilized by means of a tempering step T at 500° C. Moreover, an intermediate layer of titanium can also be applied between the two layers 2, 3 during the physical sputtering on of the gold and chrome layers.

LIST OF REFERENCE NUMBERS 1 carrier substrate
2 lower metallic layer
3 upper metallic layer
4 optical radiation; laser radiation
5 intermediate layer
6 point of impact
7 photosensitive resist
8 beam-shaping element

The invention claimed is:

1. A beam-shaping element for optical radiation, comprising:
 a carrier substrate; and
 a thin-layer metallization disposed on the substrate, which thin-layer metallization is structured for shaping a beam of said optical radiation and includes:
  at least two metallic layers, which, upon impingement of said optical radiation, react with each other and generate a permanent change in color in response to a certain intensity and/or an irradiation period of said optical radiation, wherein an upper layer of said two metallic layers comprises gold and a lower layer comprises chrome with a layer-thickness ratio of the lower layer to the upper layer of 1:2.5 to facilitate the permanent substantial change in color which directly identifies the beam-shaping element prior use.

2. A beam-shaping element according to claim 1, wherein the sold and chrome react with each other forming an alloy upon impingement of said optical radiation.

3. A beam-shaping element according to claim 1, wherein said reaction permanently lowers a reflectivity of said thin-layer metallization for said optical radiation.

4. A beam-shaping element according to claim 3, wherein the reflectivity of the thin-layer metallization is lowered to below 1%.

5. A beam-shaping element according to claim 1, which is designed for a wavelength of said optical radiation of 193 nm.

6. A beam-shaping element according to claim 1, wherein said carrier substrate includes quartz glass.

7. A beam-shaping element according to claim 1, wherein said thin-layer metallization is structured to form an optical diaphragm for said impinging optical radiation.

8. A beam-shaping element according to claim 1, wherein said thin-layer metallization has an overall layer thickness of $\leq 250$ nm.

9. A method for producing a beam-shaping element for optical radiation, comprising at least the following steps:
 application of a lower layer of chrome on a carrier substrate which is transparent for said optical radiation,
 application of an upper layer of gold over said lower layer, with said upper layer of gold and said lower layer of chrome being applied with a layer-thickness ratio of said lower layer to said upper layer of 1:2.5 to facilitate a visible change in color to identify usage of the beam-shaping element,
 microstructuring of said upper layer by means of photolithography and a subsequent dry etching process, and
 microstructuring of said lower layer by means of a wet-etching process, in which said upper layer acts as an etching mask.

10. A method according to claim 9, wherein said lower layer and said upper layer are applied using a physical sputtering method.

11. A method according to claim 9, wherein before application of said upper layer an intermediate layer of titanium is applied onto said lower layer.

12. A method according to claim 11, wherein said applied layers are thermodynamically stabilized by means of a thermal aging process.

* * * * *